United States Patent [19]

Sachau et al.

[11] Patent Number: 5,147,344
[45] Date of Patent: Sep. 15, 1992

[54] HYDROGEL FOAMS, AND A PROCESS FOR THEIR PREPARATION

[75] Inventors: Günther Sachau, Quickborn; Katrin Borgschulte; Hanns Pietsch, both of Hamburg, all of Fed. Rep. of Germany

[73] Assignee: Beiersdorf Aktiengesellschaft, Hamburg, Fed. Rep. of Germany

[21] Appl. No.: 664,904

[22] Filed: Mar. 5, 1991

[30] Foreign Application Priority Data

Mar. 10, 1990 [DE] Fed. Rep. of Germany ....... 4007668

[51] Int. Cl.$^5$ .................... A61F 13/15; B01J 13/00; A61K 9/66

[52] U.S. Cl. .................... 604/368; 252/307; 252/315.1; 424/445; 424/449; 424/488; 521/141; 604/369

[58] Field of Search ............ 252/307, 315.1; 424/315.1, 445, 449; 604/368, 369; 521/141

[56] References Cited

U.S. PATENT DOCUMENTS

| | | | |
|---|---|---|---|
| 4,432,798 | 2/1984 | Helferich et al. | 106/38.3 |
| 4,919,939 | 4/1990 | Baker | 424/493 |
| 4,948,575 | 9/1990 | Cole et al. | 424/44 |
| 5,039,540 | 8/1991 | Ecanow | 426/385 |

*Primary Examiner*—Richard D. Lovering
*Assistant Examiner*—N. Bhat
*Attorney, Agent, or Firm*—Sprung Horn Kramer & Woods

[57] ABSTRACT

Hydrogel foams
a) based on gelatin and water,
b) optionally containing polyvinyl alcohol,
c) containing a crosslinking agent selected from the group comprising
  ca) the compounds of at least trivalent metals or semimetals, for example boric acid, borates, aluminium salts, titanates and alkyl titanates, and/or from the group comprising
  cb) organic and/or inorganic acids and/or salts thereof, for example gallic acid, gallates, phosphoric acids, phosphates, dihydroxybenzoic acid and dihydroxybenzoates,
d) and optionally containing organic plasticizers, and/or auxiliary agents and/or additives.

10 Claims, No Drawings

HYDROGEL FOAMS, AND A PROCESS FOR THEIR PREPARATION

DESCRIPTION

The invention relates to hydrogel foams, in particular those for medical applications, and to a process for their preparation.

Hydrogels are macromolecular, natural or synthetic substances which, due to a high content of hydrophilic groups, are capable of absorptively binding water. The water-absorption capacity of many hydrogels is many times the inherent weight of the anhydrous substance.

Hydrogels are employed in many forms in medicine. They are particular suitable for dressing wounds; they have the ability to
  protect wounds against drying out
  absorb wound secretions
  act as a matrix for active ingredients of all types and
  act as the basis for colonisation with autologous or heterologous skin cells.

Hydrogels can be used, inter alia, in the form of foams.

Foams for dressing skin wounds or surgical wounds are known per se. These are principally polyurethane foams or collagen foams.

However, the hydrogels of the prior art have various disadvantages:

Due to their hydrophilicity, most of the substances in question are water-soluble. This is usually undesired, since products of this type are not shape-stable. In addition, products of this type dissolve, in an undesired manner, at the site of use and are then no longer available for the intended purpose.

Other products are distinguished by considerable polymer crosslinking. Although some of the disadvantages of the abovementioned class of substances are thereby avoided, the swellability of these substances is, however, substantially limited or lost. In addition, the synthetic crosslinking agents employed here are all toxic to a varying extent.

EP-A-0 097 846 describes wound-treatment agents based on hydrogels. In these, gelatin, in solid form, as a powder, flakes or sheets, is reacted in a two-phase reaction with crosslinking agents, such as formaldehyde, glyoxal, glutaraldehyde, dicarboxylic acid chlorides and/or diisocyanates.

In this reaction, the crosslinking agents act on the swollen, undissolved gelatin. This process and the products obtained therefrom have considerable disadvantages, since the crosslinking agents used can cause considerable cell damage.

Moreover, the process can only be reproduced with difficulty or not at all. The crosslinking depends not only on the concentration of the crosslinking agents used, but also on parameters such as temperature and contact time of the reactants. Furthermore, the effective surface area and the mean molecular weight of commercially available gelatin grades vary considerably, and the properties of the crosslinked hydrogel are therefore difficult to predict.

Furthermore, EP-A-0 097 846 describes a bandage material comprising hydrogels based on polyvinyl alcohol. The crosslinking agent employed is formaldehyde, which, as mentioned in the introduction, is physiologically unacceptable.

Also known and customary are foams comprising polyvinyl alcohol or collagen. However, since their matrix substances have the above-described disadvantages, they are at best of limited suitability for wound dressing.

The object of the invention was therefore to develop hydrogel foams which do not have the disadvantages of the prior art and are suitable as wound dressings. In addition, it should be accomplished to prepare the foams economically by reproducible processes.

Surprisingly, it has been found that hydrogel foams
  a) based on gelatin and water,
  b) optionally containing polyvinyl alcohol,
  c) containing a crosslinking agent selected from the group comprising
    ca) the compounds of at least trivalent metals or semimetals, for example boric acid, borates, aluminium salts, titanates and alkyl titanates, and/or from the group comprising
    cb) organic and/or inorganic acids and/or salts thereof, for example gallic acid, gallates, phosphoric acids, phosphates, dihydroxybenzoic acid and dihydroxybenzoates,
  d) and optionally containing organic plasticizers, and/or auxiliary agents and/or additives, overcome the disadvantages of the prior art and clearly surpass the properties of the products thereof.

Although it is known per se that addition of boric acid increases the viscosity of polyvinyl alcohol (for example Hoechst company publication Mowiol, from 1984), there is, however, no indication anywhere that the crosslinking agents according to the invention have any crosslinking action whatsoever. In connection with the hydrogel foams according to the invention, the substances are nevertheless referred to below as "crosslinking agents".

Neither could it have been predicted that the compositions according to the invention give rise to foams. As demonstrated by means of Comparative Example 1, foams are not obtained using polyvinyl alcohol and a crosslinking agent according to the invention alone, without addition of gelatin.

The hydrogel foams according to the invention preferably contain
0.01%–20.0% by weight of crosslinking agent,
0.1%–30.0% by weight of gelatin,
30.0%–0.0% by weight of polyvinyl alcohol,
0.0%–50.0% by weight of organic plasticizer and,
50.0%–90.0% by weight of water and up to about 20% by weight of auxiliary agents and additives, based on the total weight of the composition.

The hydrogel foams according to the invention particularly preferably contain
0.01%–10.0% by weight of crosslinking agent,
1.0%–15.0% by weight of gelatin,
15.0%–1.0% by weight of polyvinyl alcohol,
5.0%–30.0% by weight of organic plasticizer and,
50.0%–80.0% by weight of water and
up to about 25% by weight of auxiliary agents and additives, based on the total weight of the composition.

The hydrogel foams according to the invention very particularly preferably contain
0.05%–5.0% by weight of crosslinking agent,
2.0%–15.0% by weight of gelatin,
15.0%–2.0% by weight of polyvinyl alcohol,
10.0%–30.0% by weight of organic plasticizer and,
50.0%–80.0% by weight of water and
up to about 20% by weight of auxiliary agents and additives, based on the total weight of the composition.

As a degradation product of collagen, the gelatin may have quite different molecular weights, depending on the degree of degradation. Depending thereon, the various types of gelatin have different jelly strengths, which are usually expressed in so-called "bloom grades".

The jelly strength is determined by loading a gelatin plate which contains 6⅔% by weight of air-dried (i.e. still moist) gelatin and has stood at 18° C. for 10 hours, with a ½ inch diameter tup, which penetrates into the gelatin. The gelatin has a jelly strength of 1 bloom grades if a weight of 1 gram on the tup causes a penetration depth of 4 mm.

The hydrogel foams according to the invention can be prepared using any commercially available gelatin type having a jelly strength of 30–300 bloom grades.

Polyvinyl alcohols are commercially available, for example under the tradenames Polyviol[R] or Mowiol[R] These are polymeric compounds of the general formula

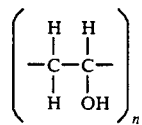

In this formula, n may be chosen according to the invention in such a manner that the polyvinyl alcohol is in the molecular weight range from 10,000 to 250,000.

Preferred crosslinking agents are, in particular, borax and potassium aluminium sulfate (potassium alum), but also the various boric acids and other alums, for example iron alum, are highly suitable according to the invention. Of the phosphoric acids, ortho-phosphoric acid is preferred.

Further favourable crosslinking agents are magnesium sulfate, aluminium sulfate, dihydroxybenzoic acid and the salts thereof, gallic acid and gallates, vanadium (III) chloride and aluminium hydroxide acetate.

Even the other crosslinking agents mentioned result in extremely advantageous embodiments of the present invention. Of the alkyl titanates, tetraethyl orthotitanate has proven preferable.

The crosslinked hydrogels may contain up to 50%, based on the dry substance, of plasticizers, preferably liquid polyols, the preferred polyol having the lowest cytotoxicity being glycerol. Other polyols which have a certain cytotoxicity per se may nevertheless be advantageously employed if they are more compatible with the crosslinked hydrogels, for example: ethylene glycol, liquid polyethylene glycols of various molecular weight, 1,2-propylene glycol, liquid poly-1,2-propylene glycols of various molecular weight, 1,3-propylene glycol, liquid poly-1,3-propylene glycols of various molecular weight, triethyl or trimethyl citrate, methyl or ethyl lactate, methyl or ethyl glycolate or 2-ethyl-2(hydroxymethyl)-1,3-propanediol.

Advantageous plasticizers are, in particular, also mono-, di- or oligosaccharides, preferably cane sugar or sorbitol.

These compounds protect the hydrogels according to the invention against drying out. This is particularly favourable if the finished hydrogel is not packaged in a water-tight or water vapour-impermeable manner.

It may be pointed out that the commercial products, in particular the gelatin and the polyvinyl alcohol, but also the crosslinking agents and the plasticizers, have a certain water content as a consequence of their processing. Unless otherwise stated, references to the individual substances denote the dry pure substance.

The hydrogel foams according to the invention are prepared by first stirring the hydrogel base, i.e. gelatin, or a mixture of gelatin and polyvinyl alcohol, with water and, if desired, the plasticizer. It is advantageous here to warm the mixture, preferably to temperatures of 60°–100° C., in particular to temperatures of 70°–95° C. The crosslinking agent is added to the solution obtained in this way. A stream of gas is passed through the reaction mixture which should be vigorously stirred. The foam which forms after some time can be further processed, for example spread to form sheet-like structures.

Preference is given to the process for the preparation of hydrogel foams in which gelatin, or a mixture of gelatin and polyvinyl alcohol, is stirred with water, and, if desired, the plasticizer, the crosslinking agent is added to the mixture obtained in this way, the reaction mixture produced in this way is stirred vigorously, stream of gas is passed through the reaction mixture, and the foam produced in this way is, if desired, spread to form sheet-like structures or, if desired, applied to a sheet-like substrate.

The hydrogel foams according to the invention may particularly advantageously be applied by processes known per se to sheet-like substrates, for example woven fabrics, knitted fabrics, nonwovens, films or the like. The coated substrates obtained in this way may in addition be provided with a contact adhesive.

It is also possible, and advantageous, to produce articles from the hydrogel foams according to the invention which are not sheet-like, but instead have a pronounced three-dimensional structure.

The finished foam, preferably the above-described sheet-like structures but advantageously also the substrates coated with hydrogel foam, may be used, for example, to dress surface wounds or surgical wounds.

The examples below are intended to illustrate the invention, but there is no intention to limit the invention to these examples.

EXAMPLE 1

A mixture of 4 parts by weight of gelatin (containing about 10% by weight of water), 7 parts by weight of polyvinyl alcohol (molecular weight about 75,000), 73 parts by weight of water and 16 parts by weight of glycerol (containing about 15% by weight of water) is heated at 85°–90° for 2 hours with stirring. A solution forms, to which 0.1 part by weight of borax is then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained which can be spread to form leaves with a thickness of about 1 mm.

EXAMPLE 2

A mixture of 4 parts by weight of gelatin (containing about 10% by weight of water), 7 parts by weight of polyvinyl alcohol (molecular weight about 75,000), 64.5 parts by weight of water and 23 parts by weight of sorbitol (containing about 30% by weight of water) is heated at 85°–90° C. for 2 hours with stirring. A solution forms, to which 1.5 parts by weight of potassium aluminium sulfate are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

EXAMPLE 3

A mixture of 4 parts by weight of gelatin (containing about 10% by weight of water), 7 parts by weight of polyvinyl alcohol (molecular weight about 75,000), 68 parts by weight of water, 11.5 parts by weight of sorbitol (containing about 30% by weight of water) and 16 parts by weight of glycerol (containing about 15% by weight of water) heated at 85°-90° C. for 2 hours with stirring. A solution forms, to which 1.5 parts by weight of potassium aluminium sulfate are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

EXAMPLE 4

A mixture of 4 parts by weight of gelatin (containing about 10% by weight of water), 7 parts by weight of polyvinyl alcohol (molecular weight about 75,000), 74.2 parts by weight of water and 14 parts by weight of sucrose is heated at 85°-90° C. for 2 hours with stirring. A solution forms, to which 0.7 part by weight of potassium aluminium sulfate and 0.1 part by weight of borax are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

EXAMPLE 5

A mixture of 4 parts by weight of gelatin (containing about 10% by weight of water), 7 parts by weight of polyvinyl alcohol (molecular weight about 75,000), 72.2 parts by weight of water and 16 parts by weight of glycerol (containing about 15% by weight of water) is heated at 85°-90° C. for 2 hours with stirring. A solution forms, to which 0.8 part by weight of tetraethyl titanate are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

EXAMPLE 6

A mixture of 8 parts by weight of gelatin (containing about 10% by weight of water), 7 parts by weight of polyvinyl alcohol (molecular weight about 75,000), 72.9 parts by weight of water and 12 part by weight of glycerol (containing about 15% by weight of water) is heated at 85°-90° C. for 2 hours with stirring. A solution forms, to which 0.1 part by weight of borax are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

Example 7

A mixture of 2 parts by weight of gelatin (containing about 10% by weight of water), 8 parts by weight of polyvinyl alcohol (molecular weight about 75,000), 70.5 parts by weight of water and 16 parts by weight of glycerol (containing about 15% by weight of water) is heated at 85-90° C for 2 hours with stirring. A solution forms, to which 3.5 parts by weight of potassium aluminium sulfate are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

EXAMPLE 8

A mixture of 11 parts by weight of gelatin (containing about 10% by weight of water), 72.9 parts by weight of water and 16 parts by weight of glycerol (containing about 15% by weight of water) is heated at 85°-90° C. for 2 hours with stirring. A solution forms, to which 0.1 part by weight of borax are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

EXAMPLE 9

A mixture of 4 parts by weight of gelatin (containing about 10% by weight of water), 7 parts by weight of polyvinyl alcohol (molecular weight about 75,000), 72.4 parts by weight of water and 16 parts by weight of glycerol (containing about 15% by weight of water) is heated at 85°-90° C. for 2 hours with stirring. A solution forms, to which 0.6 part by weight of gallic acid are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

EXAMPLE 10

A mixture of 4 parts by weight of gelatin (containing about 10% by weight of water), 7 parts by weight of polyvinyl alcohol (molecular weight about 75,000), 71.5 parts by weight of water, 14 parts by weight of glycerol (containing about 15% by weight of water) and 2% by weight of panthenol is heated at 85°-90° C. for 2 hours with stirring. A solution forms, to which 1.5 parts by weight of potassium aluminium sulfate are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

EXAMPLE 11

A mixture of 4 parts by weight of gelatin (containing about 10% by weight of water), 7 parts by weight of polyvinyl alcohol (molecular weight about 75,000), 71.5 parts by weight of water, 13 parts by weight of glycerol (containing about 15% by weight of water) 1.5% by weight of panthenol and 1.5% by weight of ascorbyl palmitate is heated at 85°-90° C. for 2 hours with stirring. A solution forms, to which 1.5 parts by weight of potassium aluminium sulfate are then added. After a further hour, the bath temperature is reduced to 60° C. The stirring speed is set at 1,000 revolutions/minute. A continuous stream of gas is passed through the mixture for a period of 2 hours during this operation.

A spreadable foam is obtained, which can be spread to give leaves with a thickness of about 1 mm.

COMPARATIVE EXAMPLE 1

A mixture of 11 parts by weight of polyvinyl alcohol (molecular weight about 75,000), 64.5 parts by weight of water and 23 parts by weight of sorbitol (containing about 30% by weight of water) is heated at 85°14 90° C. for 2 hours with stirring. A solution forms, to which 1.5 parts by weight of potassium aluminium sulfate are then added. After a further hour, the bath temperature is reduced to 60° C. The stirring speed is set at 1,000 revolutions/minute. A continuous stream of gas is passed through the mixture for a period of 2 hours during this operation.

No foam is obtained.

We claim:

1. A hydrogel foam comprising by weight
   0.01%-20.0% of at least one crosslinking agent selected from the group consisting of
   i) a compound of an at least trivalent metal or semimetal and
   ii) an organic or inorganic acid or salt thereof,
   0.01%-30.0% of gelatin,
   30.0%-0.0% of polyvinyl alcohol,
   0.0%-50.0% of an organic plasticizer,
   50.0%-90.0% of water and
   0 to about 20% of at least one auxiliary agent or additive.

2. A hydrogel foam according to claim 1, comprising by weight
   0.01%-10.0% of a crosslinking agent,
   0.1%-15.0% of gelatin,
   15.0%-1.0% of polyvinyl alcohol,
   5.0%-30.0% of an organic plasticizer,
   50.0%-80.0% of water and
   up to about 25% of at least one auxiliary agent or additive.

3. A hydrogel foam according to claim 1, comprising by weight
   0.05%-50.0% of a crosslinking agent,
   2.0%-15.0% of gelatin,
   15.0%-2.0% of polyvinyl alcohol,
   10.0%-30.0% of an organic plasticizer,
   50.0%-80.0% of water and
   up to about 25% of at least one auxiliary agent or additive.

4. A hydrogel foam according to claim 1, wherein the crosslinking agent is selected from the group consisting of borax, boric acid, tetraethyl orthotitanate, orthophosphoric acid and potassium aluminium sulfate.

5. A hydrogel foam according to claim 1, wherein the crosslinking agent is acidic.

6. A hydrogel foam according to claim 1, wherein the crosslinking agent comprises at least one member selected from the group consisting of boric acid, a borate, an aluminium salt, a titanate and an alkyl titanate.

7. A hydrogel foam according to claim 1, wherein the crosslinking agent comprises at least one member selected from the group consisting of gallic acid, a gallate, phosphoric acid, a phosphate, dihydroxybenzoic acid and a dihydroxybenzoic acid salt.

8. A sheet-like support carrying a hydrogen foam according to claim 1.

9. A process for the preparation of a sheet-like structure according to claim 8, comprising:
   a) stirring with water gelatin and the polyvinyl alcohol if included,
   b) adding thereto the crosslinking agent,
   c) stirring vigorously,
   d) passing a stream of gas therethrough, and
   e) applying the mass to a support.

10. In the application to the skin of a sheet-like structure carrying a hydrogel foam, the improvement which comprises employing as said structure a structure according to claim 8.

* * * * *

UNITED STATES PATENT AND TRADEMARK OFFICE
CERTIFICATE OF CORRECTION

PATENT NO. : 5,147,344

DATED : September 15, 1992

INVENTOR(S) : Sachau et al.

It is certified that error appears in the above-identified patent and that said Letters Patent is hereby corrected as shown below:

Col. 7, line 39   Delete " 0.01 " and substitute -- 0.1 --

Col. 8, line 32   Delete " hydrogen " and substitute -- hydrogel --

Signed and Sealed this

First Day of February, 1994

*Attest:*

BRUCE LEHMAN

*Attesting Officer*          *Commissioner of Patents and Trademarks*